US011703513B2

(12) United States Patent
Hughes et al.

(10) Patent No.: US 11,703,513 B2
(45) Date of Patent: *Jul. 18, 2023

(54) SYSTEMS AND METHODS FOR ENZYMATIC A1C DETECTION AND QUANTIFICATION

(71) Applicant: Polymer Technology Systems, Inc., Indianapolis, IN (US)

(72) Inventors: Gary Hughes, Camby, IN (US); Ryan Jesswein, Indianapolis, IN (US); Brittney Werner, Beech Grove, IN (US); Aniruddha Patwardhan, Fishers, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/670,481

(22) Filed: Aug. 7, 2017

(65) Prior Publication Data

US 2019/0041406 A1 Feb. 7, 2019

(51) Int. Cl.
| | | |
|---|---|---|
| *G01N 33/72* | (2006.01) | |
| *G01N 33/543* | (2006.01) | |
| *C12N 9/06* | (2006.01) | |
| *A61B 5/1486* | (2006.01) | |

(Continued)

(52) U.S. Cl.
CPC ......... *G01N 33/723* (2013.01); *A61B 5/1486* (2013.01); *C12N 9/0022* (2013.01); *C12N 9/0032* (2013.01); *G01N 33/5438* (2013.01); *A61B 5/14532* (2013.01);
(Continued)

(58) Field of Classification Search
CPC ........... G01N 33/558; G01N 33/54387; G01N 33/54388; G01N 33/54389; G01N 33/723; G01N 33/5438; G01N 27/327; G01N 27/3271; G01N 27/3272; G01N 33/49; G01N 33/52; B01L 2300/0825; A61B 5/1486; A61B 5/14532; A61B 5/14542; A61B 5/150358; A61B 2562/0295; C12N 9/0022; C12N 9/0032; C12Y 105/03;
(Continued)

(56) References Cited

U.S. PATENT DOCUMENTS

| | | | |
|---|---|---|---|
| 5,695,949 A | 12/1997 | Galen et al. | |
| 6,773,671 B1 * | 8/2004 | Lewis | G01N 33/521 |
| | | | 422/169 |
| 2004/0265941 A1 | 12/2004 | Galen et al. | |

(Continued)

FOREIGN PATENT DOCUMENTS

| | | |
|---|---|---|
| CN | 1215168 A | 4/1999 |
| CN | 1244259 A | 2/2000 |

(Continued)

OTHER PUBLICATIONS

Machine Translation of JP2014102144A, 7 pages. (Year: 2014).*

(Continued)

*Primary Examiner* — Christopher L Chin
(74) *Attorney, Agent, or Firm* — Haynes and Boone, LLP

(57) ABSTRACT

A system for determining a concentration of hemoglobin A1C includes a first electrochemical test strip, the first electrochemical test strip providing for an HbA1C concentration; and a second electrochemical test strip, the second electrochemical test strip providing for the total amount of hemoglobin.

10 Claims, 6 Drawing Sheets

(51) Int. Cl.
   *A61B 5/15* (2006.01)
   *A61B 5/145* (2006.01)
(52) U.S. Cl.
   CPC ..... *A61B 5/14542* (2013.01); *A61B 5/150358* (2013.01); *A61B 2562/0295* (2013.01); *C12Y 105/03* (2013.01)
(58) Field of Classification Search
   CPC ........ C12Q 1/001; C12Q 1/004; C12Q 1/005; C12Q 1/37
   USPC .............. 204/403.11, 403.04, 403.1, 403.14; 422/82.11, 400, 401, 420, 421, 425, 426, 422/430; 435/287.7, 287.9, 970, 805, 435/810, 817; 436/66, 67, 169, 170, 514, 436/518, 530, 806, 810
   See application file for complete search history.

(56) References Cited

U.S. PATENT DOCUMENTS

| | | | |
|---|---|---|---|
| 2006/0030050 A1 | 2/2006 | Milne et al. | |
| 2006/0113187 A1* | 6/2006 | Deng | C12Q 1/005 204/403.01 |
| 2008/0233605 A1* | 9/2008 | Taniguchi | G01N 33/726 435/23 |
| 2009/0221431 A1* | 9/2009 | Yoo | B01L 3/502738 506/9 |
| 2009/0308744 A1* | 12/2009 | Nam | G01N 33/5308 204/403.07 |
| 2010/0025264 A1 | 2/2010 | Yuan et al. | |
| 2010/0089774 A1* | 4/2010 | Manohar | G01N 27/3271 205/792 |
| 2011/0005941 A1 | 1/2011 | Blythe et al. | |
| 2011/0269147 A1 | 11/2011 | Chinnayelka | |
| 2012/0208226 A1 | 8/2012 | Ikebukuro et al. | |
| 2012/0296189 A1 | 11/2012 | Bhogal et al. | |
| 2013/0171028 A1 | 7/2013 | Shaffer et al. | |
| 2014/0273187 A1 | 9/2014 | Johnson et al. | |
| 2014/0370539 A1 | 12/2014 | Shen et al. | |

FOREIGN PATENT DOCUMENTS

| | | | |
|---|---|---|---|
| CN | 101236192 A | | 8/2008 |
| CN | 102076867 A | | 5/2011 |
| CN | 103124793 A | | 5/2013 |
| CN | 105163661 A | | 12/2015 |
| EP | 2604698 A1 | | 6/2013 |
| JP | 2008245657 A | | 10/2008 |
| JP | 2014102144 A | * | 6/2014 |
| KR | 101541798 B1 | | 8/2015 |
| WO | WO2009140343 A1 | | 11/2009 |
| WO | WO2015060429 A1 | | 4/2015 |

OTHER PUBLICATIONS

Toyobo, Neutral Proteinase, retrieved from http://www.toyobousa.com/enzyme-NEP-801.html. 4 pages (Year: 2020).*
Liu et al., Determination of Percent Hemoglobin A1c Using a Potentiometric Method, l Anal. Chem. 2013, 85, 1834-1839. (Year: 2013).*
International Search Report and Written Opinion dated Oct. 30, 2017 issued in related PCT App. No. PCT/US2017/045716 (14 pages).
International Search Report and Written Opinion dated Feb. 12, 2018 issued in related PCT App. No. PCT/US2017/065874 (8 pages).
Suh et al., "Remarkable Proteolytic Activity of Imidazoles Attached to Cross-Linked Polystyrene," The Journal of Organic Chemistry, vol. 65, No. 22, Sep. 29, 2000 [retrieved on Jan. 26, 2018]. Retrieved from the Interent: <URL: http://pubs.acs.org/dol/abs/10.1021/jo000896q>.
Office Action dated Sep. 29, 2021 issued in related India patent application No. 201937039691 (6 pages).
Extended European Search Report dated Oct. 4, 2021 issued in related European patent application No. 17934977.4 (5 pages).
Office Action dated May 18, 2022 issued in related Chinese patent application No. 201780089687.2 (16 pages with translation).
Office Action dated Feb. 24, 2022 issued in related India patent application No. 201937039649 (6 pages).
Office Action dated Nov. 7, 2022 issued in Chinese patent application No. 201780089613.9 (23 pages).

* cited by examiner

SYSTEMS AND METHODS FOR ENZYMATIC A1C DETECTION AND QUANTIFICATION

CROSS-REFERENCE TO RELATED APPLICATION

This application claims the benefit of U.S. Provisional Application No. 62/466,983 filed on Mar. 3, 2017, which is incorporated herein by reference in its entirety.

BACKGROUND

Point of Care ("POC") and home testing for various blood analytes and other detectable metrics in bodily fluids is desirable for patient and doctor. One such analyte is A1C, a type of glycated hemoglobin. High levels of blood glucose cause over-glycation of proteins, including hemoglobin, throughout the body. Glycation of hemoglobin occurs primarily at the amino termini of beta chains, as well as other sites with free amino groups. Hemoglobin A undergoes a slow glycation with glucose that is dependent on the time-average concentration of glucose over the 120-day life span of red blood cells. The most prevalent and well-characterized species of glycated hemoglobin A is A1C, making up approximately 3% to 6% of the total hemoglobin in healthy individuals. The correlation of A1C and blood glucose levels make it a useful method for monitoring long-term blood glucose levels in people with diabetes. The mean (average) blood glucose level (MBG) is a function of the A1C levels, and is therefore derivable.

PTS manufactures the A1CNow, a Point-of-Care device for measuring HbA1c. This test is an immunochemistry (antigen-antibody) based system which performs well unless the patient has hemoglobin variances (HbS and HbC, are the two most common variants) which create false high results as much as 30%. It would be desirable to provide an assay that is not affected by these hemoglobin variances.

BRIEF SUMMARY

In one embodiment, a system for determining a concentration of hemoglobin A1C includes a first electrochemical test strip, the first electrochemical test strip providing for a percent of HbA1c concentration; and a second electrochemical test strip, the second electrochemical test strip providing for the total amount of hemoglobin. Optionally, the second electrochemical test strip includes a potassium ferricyanide solution with a lysing surfactant such as Triton X-100™, (known as t-Octylphenoxypolyethoxyethanol), such that released hemoglobin reacts with the potassium ferricyanide solution to form methemoglobin. Alternatively, the first electrochemical test strip includes a stripe with a coating of Fructosyl Amino acid oxidase (FPO-301) enzyme that acts on Fructosyl-L-Valylhistidine as substrate. In another alternative, the first electrochemical test strip includes a strip with a coating of Fructosyl Amino acid oxidase. Alternatively, the coating further includes a ruthenium hexamine trichloride mediator. In another alternative, the coating further includes derivatives a ruthenium hexamine trichloride mediator. Optionally, the coating includes a combination of organometallic species. Alternatively, the Fructosyl Amino oxidase directly transfers the electron to the mediator thus by-passing the peroxide generation step. In one configuration, each of the first and second electrochemical test strips includes a first electrode and a second electrode. In another configuration, one of the first and second electrodes includes a reagent on a surface of one of the first and second electrodes. Optionally, the reagent is painted onto the one of the first and second electrodes. Alternatively, the first and second test strips are located in a single holder. In one alternative, the single holder further includes a third test strip, the third test strip testing for an additional analyte. In another alternative, the additional analyte is selected from a list consisting of glucose, HbA1C, ketones, triglycerides, or lactate. Optionally, the single holder further includes a fourth test strip, the fourth test strip testing for a fourth analyte wherein the fourth analyte is selected from a list consisting of glucose, HbA1C, ketones, triglycerides, or lactate and is non-redundant with the additional analyte.

In another embodiment, a method for determining a concentration of hemoglobin A1C includes providing a system including a first electrochemical test strip, the first electrochemical test strip providing for a percent of HbA1C concentration; and a second electrochemical test strip, the second electrochemical test strip providing for the total amount of hemoglobin. The method further includes dosing the system with a sample; and reading the first and second electrochemical test strips to determine the percent of HbA1C concentration and the total amount of hemoglobin. In one configuration, the reading is performed by a meter. Optionally, the second electrochemical test strip includes a potassium ferricyanide solution with a lysing surfactant such as Triton X-100™ such that released hemoglobin reacts with the potassium ferricyanide solution to form methemoglobin. Alternatively, the first electrochemical test strip includes a stripe with a coating of Fructosyl Amino acid oxidase (FPO-301). Optionally, Fructosyl Amino oxidase directly transfers an electron to a mediator thus by-passing a peroxide generation step. Alternatively, the first electrochemical test strip includes a stripe with a coating of Fructosyl Amino acid oxidase enzyme and ruthenium hexamine trichloride mediator. Optionally, each of the first and second electrochemical test strips includes a first electrode and a second electrode. Alternatively, one of the first and second electrodes includes a reagent on a surface of one of the first and second electrodes. Optionally, the reagent is painted onto one of the first and second electrodes. In another configuration, the reagent is painted on both of the first and second electrodes. In one configuration, the first and second test strips are located in a single holder. In another configuration, the single holder further includes a third test strip, and the method further comprises testing for an additional analyte with the third test strip. Optionally, the additional analyte is selected from a list consisting of glucose, HbA1C, ketones, triglycerides, or lactate. Alternatively, the single holder further includes a fourth test strip, the fourth test strip testing for a fourth analyte wherein the fourth analyte is selected from a list consisting of glucose, HbA1C, ketones, triglycerides, or lactate and is non-redundant with the additional analyte.

DETAILED DESCRIPTION

Figure 1:
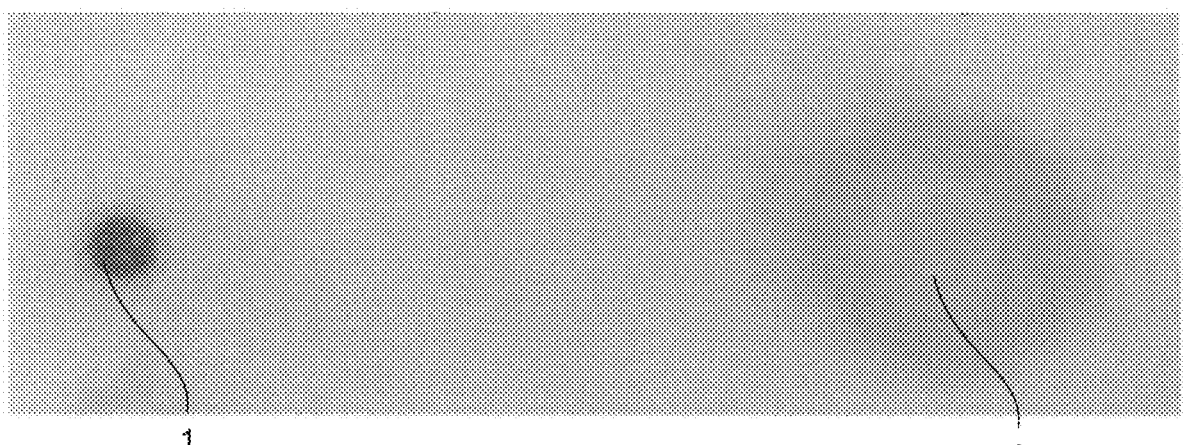
FIG. 1 shows a Dot Blot with Hemolysate as the control on the left and hemolysate with Toyobo's Neutral Proteinase on the right after 30 sec of sample digestion.

Certain terminology is used herein for convenience only and is not to be taken as a limitation on the embodiments of the systems and methods for enzymatic detection and quantification of HbA1c. The enzymatic detection and quantification techniques described herein enable electrochemical detection of HbA1c. In the drawings, the same reference letters are employed for designating the same elements throughout the several figures. Such a detection scheme provides for the elimination of variances due to genetic differences in individuals, providing for greater accuracy.

PTS manufactures the A1c Now, a Point-of-Care (POC) device for measuring HbA1c. This test is an immunochemistry (antigen-antibody) based system which performs well unless the patient has hemoglobin variances (HbS and HbC, are the two most common variants) which create false high results as much as 30%.

In one embodiment, by providing a method to enzymatically measure HbA1c, the hemoglobin variance problem is eliminated. With the ever-tightening standards on HbA1c measurement by NGSP (National Glycemic Standard Program), obtaining better accuracy is a significant gain for PTS Diagnostics.

In many embodiments, an electrochemical system that will allow for HbA1c to be measured. The use of an enzyme may be included in the electrochemical analysis scheme. Provided herein is a reaction scheme and secondly, the electrochemical method to measure this reaction. Advantages of this methodology, include:

1. Being able to measure HbA1c enzymatically enables a more accurate measurement by not having hemoglobin variances pose an issue to the assay. This allows for easier NGSP certification and most importantly, better accuracy for our customers.

2. The thought of an enzymatic approach to HbA1c measurement is a relatively new field, but it eliminates many of the issues with antigen-antibody based systems.

3. An electrochemical HbA1c approach is novel, allowing for a versatile meter that can test many different analytes. In addition, the HbA1c assay can be combined with other assays to create a multi-analyte amperometric test strip.

4. An advantage of enzymatically measuring HbA1c is the accuracy it will provide. The hemoglobin variances that are more likely in certain ethnic populations cause false high results in the current assay. By eliminating the error from the hemoglobin variances, the accuracy will dramatically increase, allowing for easier NGSP certification and better results for the patient.

5. The enzymes that we are suggesting are relatively cheap and commercially available.

Hemoglobin A1c is formed when glucose binds to the N-terminal valine residue of the β-chains of hemoglobin. The percentage of HbA1c in total hemoglobin tells the tale of the last three months of average glucose measurements. It is an indicator of how well or how poorly a diabetic has controlled their diabetes and can also be an indicator of pre-diabetes.

Measuring glycated hemoglobin (HbA1c) via enzymes is a fairly new field. The systems and methods herein leverage the efforts that others have made in developing novel enzymes for binding with glycated hemoglobin. To our knowledge, an enzymatic POC device has not been invented for HbA1c. It is our intention to present the science and the way of creating such an assay that we believe will revolutionize this field.

Enzyme Methodology

In one embodiment, an enzymatic path to measuring HbA1c begins with a well known process of degrading hemoglobin selectively by employing a protease. This protease is capable of degrading glycated hemoglobin selectively to a glycated hemoglobin degradation product(s) fructosyl-valylhistidine (F-VH) or fructosyl-valine (F-V). Toyobo's Neutral Proteinase (NEP-801) is a choice protease for this reaction. The reaction is seen below.

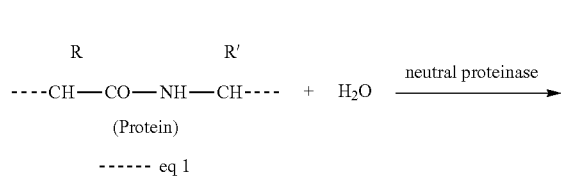

The results of proteolytic step is demonstrated in FIG. 1. FIG. 1 shows a Dot Blot with Hemolysate as the control 1 on the left and hemolysate with Toyobo's Neutral Proteinase 2 on the right. The spread out signature on the right, demonstrates the rapid and efficient proteolytic activity of Toyobo's Neutral Proteinase. The results shown are after approximately 30 seconds of reaction.

This proteolytic digestion of the HbA1c releases a fructosyl-L-amino acid, which is acted upon by Toyobo's Fructosyl-amino acid oxidase (FPO-301) (see reaction below).

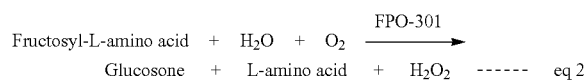

A theoretical calculation performed (Table 1) shows the relationship of fructosyl valylhistidine formed at pathological limits from 4 to 17% HbA1c to the various levels of hemoglobin concentrations in a sample.

TABLE 1

Shows the theoretical levels of Fructosyl-ValylHistidine formed at various % HbA1c and hemoglobin levels.

| Hemoglobin Range g/dL | Hemoglobin mMol/L | 4% HbA1c in mM HbA1c | 17% HbA1c in mM HbA1c | 4% HbA1c in mM F-VH | 17% HbA1c in mM F-VH |
|---|---|---|---|---|---|
| 8  | 4.95  | 0.20 | 0.84 | 0.40 | 1.68 |
| 10 | 6.18  | 0.25 | 1.05 | 0.49 | 2.10 |
| 12 | 7.42  | 0.30 | 1.26 | 0.59 | 2.52 |
| 14 | 8.65  | 0.35 | 1.47 | 0.69 | 2.94 |
| 16 | 9.89  | 0.40 | 1.68 | 0.79 | 3.36 |
| 18 | 11.13 | 0.45 | 1.89 | 0.89 | 3.78 |
| 20 | 12.36 | 0.49 | 2.10 | 0.99 | 4.20 |

Electrochemical Enzymatic HbA1c

1. Hemoglobin

Measuring HbA1c in many embodiments, necessitates a total hemoglobin measurement as well as an HbA1c measurement in order to obtain a percentage of HbA1c. One of the standard methods of measuring hemoglobin is Drabkin's Reagent. This classic approach is based on the oxidation of hemoglobin in the presence of alkaline potassium ferricyanide to methemoglobin. The methemoglobin is then reacted with potassium cyanide to form cyanmethemoglobin for the purpose of absorbance readings. The cyanomethemoglobin concentration is read using a light source at 540 nm and is proportional to the total hemoglobin concentration. The Drabkin's Reagent hemoglobin assay is typically conducted with 5 mL of reagent and 20 μL of blood. This allows for the lysing of the RBCs (Red Blood Cells) and the red color from the blood to be diluted.

According to some embodiments, measuring total hemoglobin could be performed electrochemically. In one embodiment, an electrochemical strip with a potassium ferricyanide solution with a lysing surfactant such as Triton X-100™ is provided. In various alternatives other surfactants or lysing agents may be used. The released hemoglobin reacts with the ferricyanide to form methemoglobin. After a predetermined time interval, a potential is applied and the resulting ferrocyanide is reacted at the electrode according to the below equation.

$Fe^{2+}$ globin (hemoglobin)+$K^3Fe^{3+}$ (CN)6 (ferricyanide)→$Fe^{3+}$ globin (methemoglobin)+$K^4F^{2+}$(CN)$_6$ (ferrocyanide)

Measuring hemoglobin electrochemically has certain advantages over using the Drabkin's Reagent or other optical based assays. First, measuring hemoglobin electrochemically requires no dilution step. A dilution step is prone to sampling errors and is simply one more step for the user. Additionally, this method is preferred over because it does not have the error associated with the entrapment of air bubbles in the micro cuvettes. Additionally, any time reflectance or other light based detection schemes are used, there are parts of the blood, such as the hematocrit that may interfere with the light detections schemes. The example given above is noted as being one method of measuring hemoglobin electrochemically. Alternative techniques may be used and substituted in for this technique.

2. Hemoglobin A1c

Above is presented one embodiment of the enzyme reaction for measuring glycated hemoglobin. Embodiments of the implementation of this reaction scheme in an electrochemical system are presented below. There are some issues with converting the reaction scheme to an electrochemical platform. In one electrochemical reaction scheme, First, the glycated hemoglobin will be broken down to a fructosyl amino acid (e.g. fructosyl valylhistidine or fructosyl-valine) with the well-known protease method. Secondly, the fructosyl valylhistidine or fructosyl-valine will be acted upon by the fructosyl-amino acid oxidase. By using a ruthenium hexamine trichloride [$Ru(NH_3)Cl_3$] chloride (mediator) or other derivatives thereof as well as a combination with other organometallic species, the fructosyl-amino acid oxidase will transfer electrons directly to the mediator as shown in the reaction below. We have shown proof of concept that fructosyl valylhistidine will react with the mediator and the fructosyl amino acid oxidase at a potential of +400 mV (see FIG. 2a). In many embodiments, gold interdigitated electrodes (see FIG. 3) are used to generate a signal. As can be seen, the dose response is very linear with good correlation of 0.993 indicating an efficient transfer of electron to the mediator and to the electrode. A linear dose response assists greatly in producing a reliable assay over a wide range. Additionally, the correlation is high, suggesting that the test is accurate. A reaction scheme is show below:

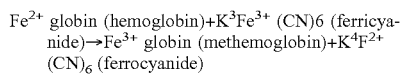
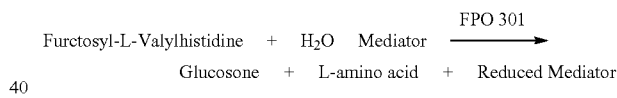

Figure 2A:
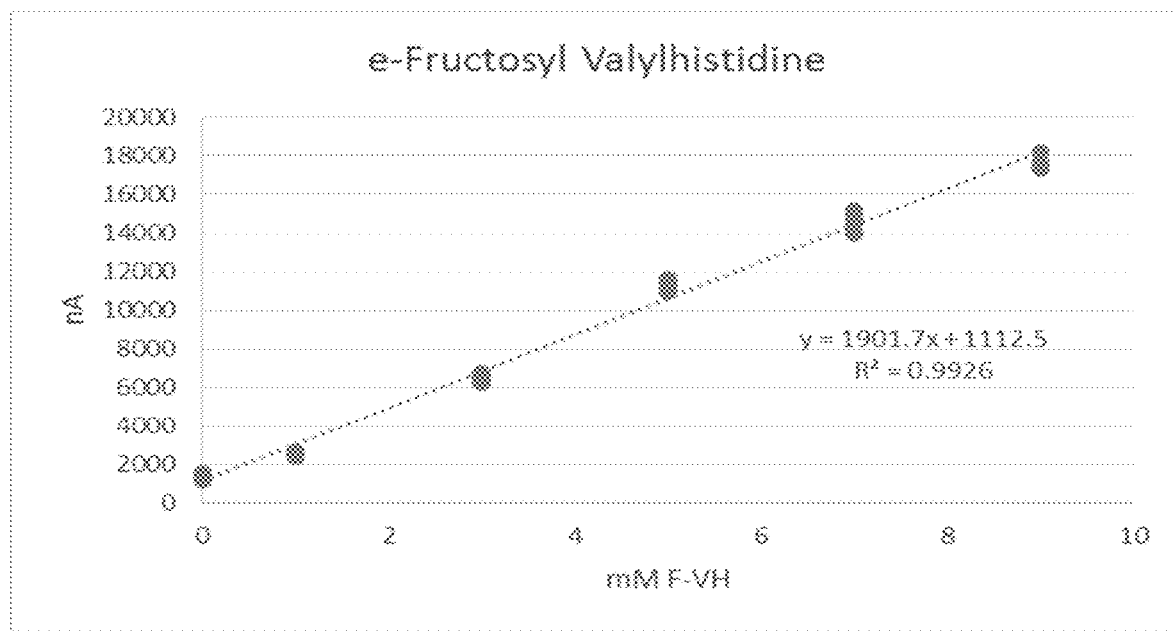
FIG. 2A shows a graph of the results of an example of a reaction of fructosyl valylhistidine on electrochemical sensors.
Figure 2B:
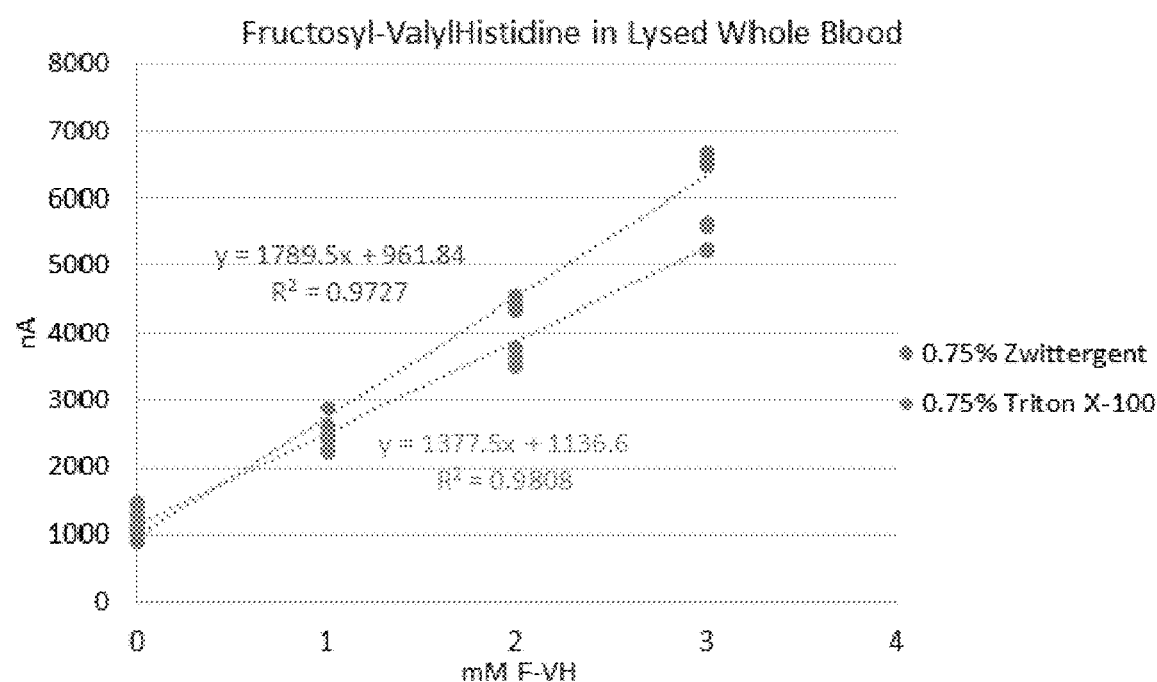
FIG. 2B shows a graph of results where the glycated degradation product fructosyl-valyl histidine in lysed whole blood yields linear dose response with either Triton X-100™ or Zwittergent 3-14™ (known as n-Tetradecyl-N,N-dimethyl-3-ammonio-1-propanesulfonate), surfactants in the RBC lysing buffer as shown in Table 1.

FIG. 2B shows a graph of results where the glycated degradation product fructosyl-valyl histidine in lysed whole blood yields linear dose response with either Triton X-100™ or Zwittergent 3-14™ surfactants in the RBC lysing buffer and preferably with Zwittergent 3-14™ surfactant. Table 2 shows two surfactant based formularies (Triton X-100™ and Zwittergent 3-14™) that are associated with FIG. 2b graph. Addition of nitrite to the formulary ensures formation of methemoglobin from oxyhemoglobin thus reducing interference and lowering the background signal. We have thus shown that fructosyl-valylhistidine substrate is able to be detected in a complex matrix like whole blood containing all of its native ingredients within the theoretical limits of fructosyl-valylhistidine formation as shown in Table 1.

TABLE 2

| Lysing Buffer # 1 Triton X-100 ™ | Lysing Buffer # 2 Zwittergent 3-14 ™ |
|---|---|
| 50 mM MES buffer | 50 mM MES buffer |
| 20 mM $NaNO_2$ | 20 mM $NaNO_2$ |
| 5 mM $CaCl_2$ | 5 mM $CaCl_2$ |
| 50 mM NaCl | 50 mM NaCl |
| 0.75% Triton X-100 ™ | 0.75% Zwittergent 3-14 ™ |

Figures 3A, 3B, 3C:
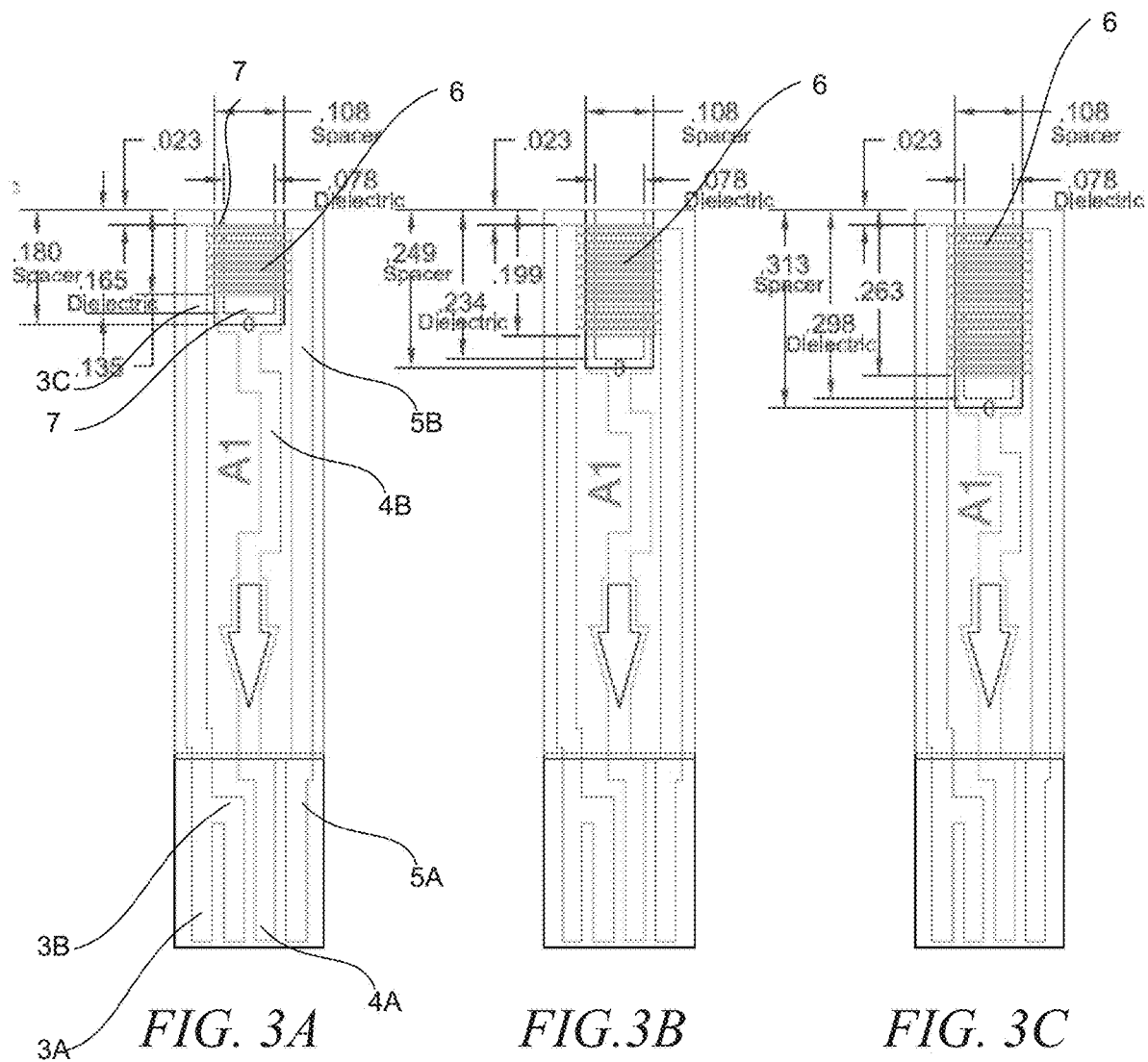
FIGS. 3A-3C show embodiments of interdigitated gold electrodes that allow for amplification of the signal produced by the Hb and HbA1c reactions.

FIGS. 2a & 2b shows graphs of the results of two example of a reaction of fructosyl valylhistidine on electrochemical sensors. In the shown examples, the sensors were interdigitated gold electrodes with an area of 0.013 square inches. Even more signal may be obtained as this data was obtained from the smallest of the interdigitated sensors (FIG. 3A). Since the amount of analyte to be detected is small, providing sensors with a large surface area and high sensitivity, more accurate and responsive measurements may be taken. Although gold electrodes may be a good choice due to their high sensitivity, other highly sensitive electrodes may be used.

FIGS. 3A-3C show embodiments of interdigitated gold electrodes that allow for amplification of the signal produced by the Hb and HbA1c reactions. By having a larger area (as shown in the progressing figures A-C) and more electrode fingers, the electrochemical signal can be magnified. As shown in FIG. 3A, an exemplary test strip including interdigitated gold electrodes. Generally, interdigitated electrodes include extremely narrow electrodes with extremely narrow interdigital gaps. In some scenarios, the electrodes are in the range of 50-500 nanometers and the interdigital gaps are in the range of 10-100 nanometers. Such an arrangement maximizes the surface area contact to the electrodes experienced by the sample. The electrodes 6 in FIGS. 3A-3C are generally not to scale, but shown as a representation of such electrodes. FIG. 3A shows three electrode leads 3A, 4A, 5A, that interface with the corresponding contacts of a meter designed to apply voltage or amperage to the strip and thereby measure the Hb and HbA1c. Electrode lead 3A includes a loop portion 3B, that allows the insertion of the test strip to be detected by the meter using a u-shaped circuit. The upper portion, interconnector 3C, interconnects to one half of the electrodes of electrodes 6. The upper portion, interconnector 5B, interconnects to the other half of the electrodes of electrodes 6, so that one half of the electrodes may function as an electrode and the other half a counter electrode. Additionally, a reference electrode interconnector 4B may be included as is typical. Dielectrics 7, as shown, surround the test area and serve to prevent current or voltage leakage during testing. Typically, dielectrics 7 comprise, glass, sitall, or other insulting ceramic. FIG. 3B and FIG. 3C show increased electrode 6 areas, which may serve to increase sensitivity.

% HbA1c Quantification: One method of calculating the final percent HbA1c is to take the ratio of the Hb and the HbA1c and convert the ratio to a percentage by the following formula:

$$\% \text{ HbA1c} = [(\text{moles of glycated hemoglobin}) \div (\text{moles of hemoglobin})] \times 100\%$$

3. Strip Design

Figure 4:
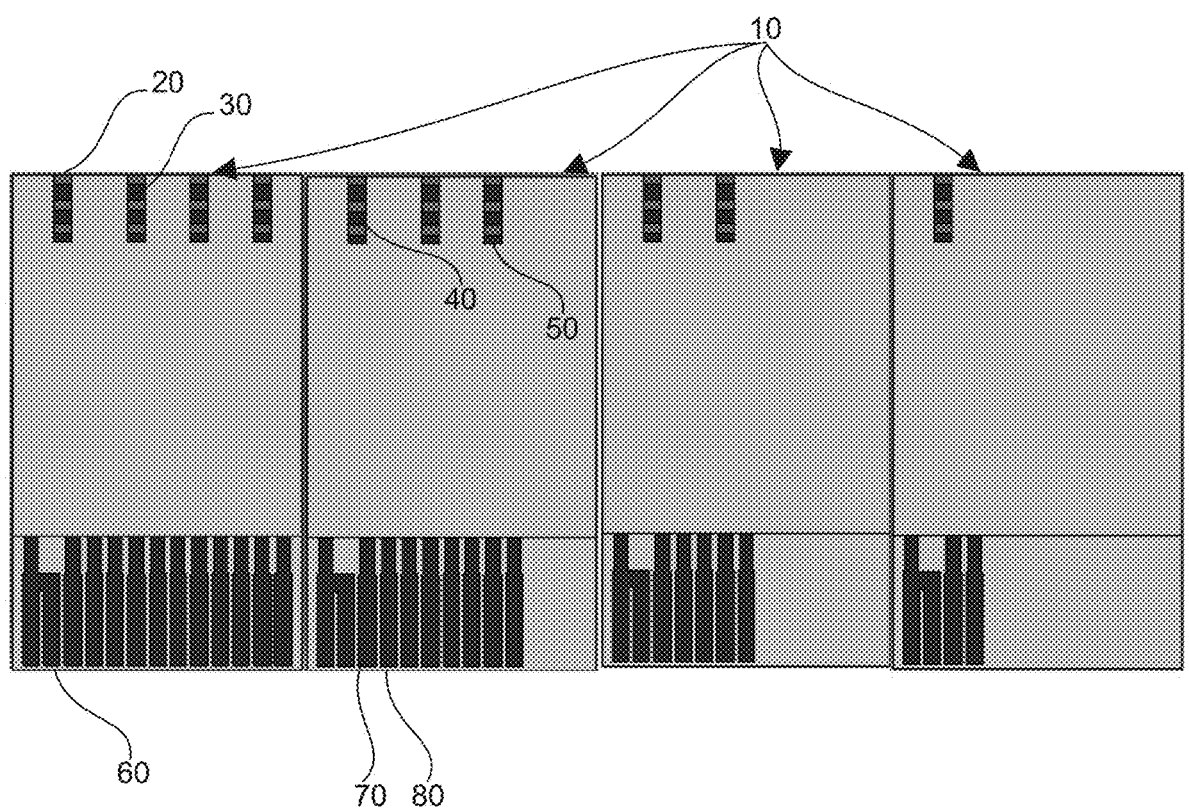
FIG. 4 shows one embodiment of a flexible electrochemical test strip having multiple single analyte tests.
Figure 5:
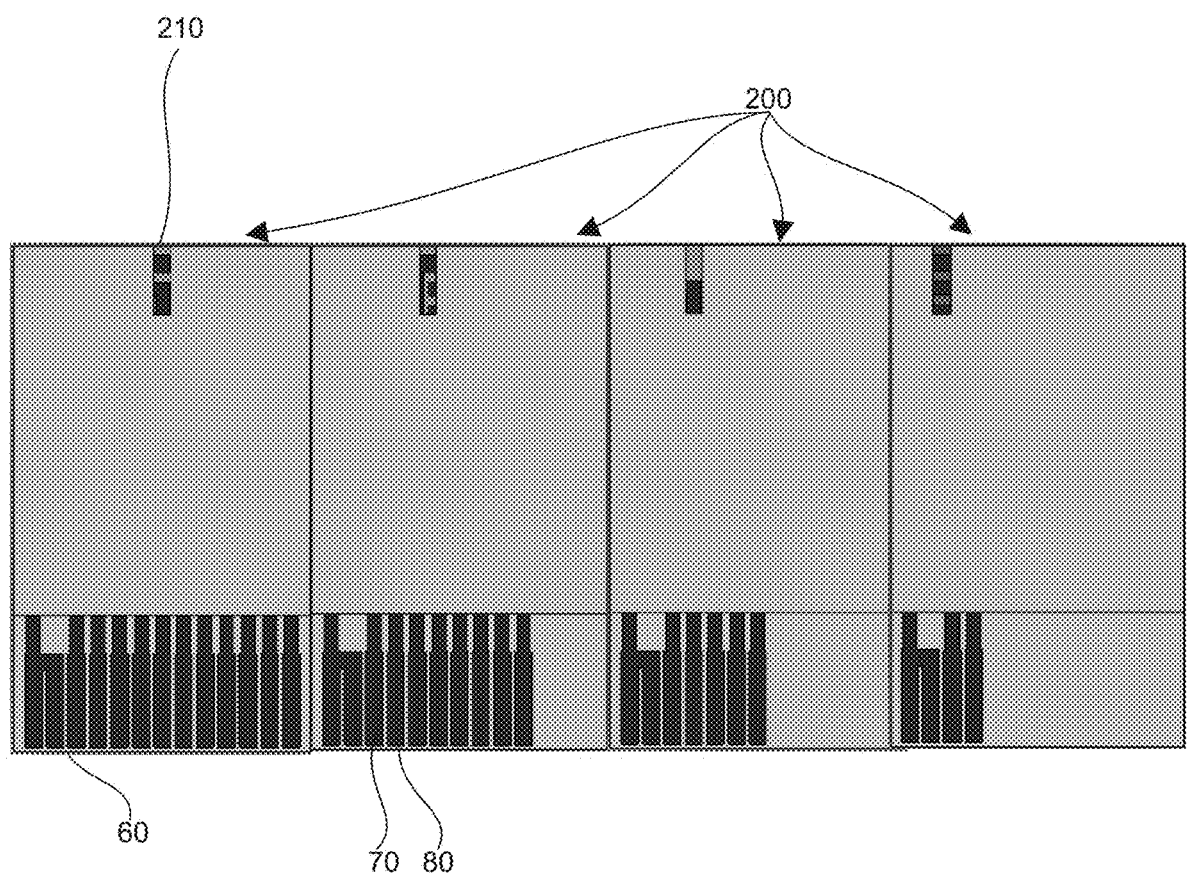
FIG. 5 shows another embodiment of a flexible electrochemical test strip having multiple analyte tests.

A versatile electrochemical test strip allowing for one or more assays to be positioned on the strip may be used. FIG. 4 shows one embodiment of the strip design. Shown are 4 strips 10. From left to right the strips 10 have 4, 3, 2, and 1 sample receiving ports 20. Each sample receiving port may have an electrode 30, a counter electrode 40, and a reference electrode 50. The reference electrode 50 may provide for a fill indication as it will only pass a voltage when the sample reaches the electrode 50. The contacts 70, 80 are also visible, which interconnect with the electrodes and connect to contacts in the meter when inserted. Electrode 60 includes an insertion check mechanism, whereby both ends of the U-shaped electrode may be used to verify that the strip has been inserted by completing a circuit from one end of the U to the other. The strip size does not change depending on the number of assays. In addition, the electrode placement does not change depending on the type of assays. Depending what is desired for the testing scheme, sheets are printed for one, two, three, or four analytes. The disclosure is not to limit the size of the panel to only four analytes, but to provide a concept that is protected whether one or 10 analytes are tested. Also, the electrodes do not all need to be on one side of the strip. Superior technology may be able to place electrodes on both sides of the strip and thus allowing for miniaturization. Depending what is required, sheets are printed for one, two, three, or four analytes. Some embodiments of this strip may include separate sampling ports particularly if there could be "cross talk" between reagents. Most likely there will be a singular sampling port for the multi-analyte panels. FIG. 5 shows such an embodiment 200. In many embodiments, there will be a singular sampling port 210 for the multi-analyte panels. Again, this strip allows for adaptability of design to meet the needs of particular assays. As shown, in the left most strip, a single sample port 210 may provide for five different sets of contacts, providing for the testing of 5 different analyte tests.

In many embodiments, an electrochemical HbA1c assay will make use of this versatile strip invention in FIG. 4. One embodiment may include a two analyte sensor HbA1c panel measuring hemoglobin and % HbA1c. However, additionally in alternatives, multiple tests may be offered including a diabetic panel, testing any of the three (or more) following combinations: glucose, HbA1c, ketones, triglycerides, or lactate. Alternatively, different configurations may be offered.

There are certain advantages of using an electrochemical platform for developing an HbA1c assay. We have listed some of them below:

The sample size will be small, usually about <5 µL per test.

A sampler or transfer pipette is not required.

Specific diagnostic membranes are not required. This eliminates pre-qualification steps of membranes and the risk that manufacturers will stop membrane production.

Calibration is of meters and is standardized to measure nA. Microchips exist that are self-calibrating.

More energy efficient than optically based systems, requiring less battery power.

Generally more precise.

Ability to "panelize" with other assays by our previous invention.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for determining a percentage glycation of hemoglobin as HbA1C, the system comprising:
a first electrochemical test strip, the first electrochemical test strip providing for an HbA1C concentration using an electrochemical analysis, wherein the first electrochemical test strip includes a strip with a coating of Fructosyl Amino acid oxidase, a ruthenium hexamine trichloride mediator, n-Tetradecyl-N,N-dimethyl-3-ammonio-1-propanesulfonate as a surfactant, and Toyobo's Neutral Proteinase (NEP-801) microbial metalloproteinase; and a second electrochemical test strip, the second electrochemical test strip providing for the total amount of hemoglobin, wherein the second electrochemical test strip includes a potassium ferricyanide solution with a lysing surfactant, the lysing surfactant being Polyethylene glycol tert-octylphenyl ether, such that released hemoglobin reacts with the potassium ferricyanide solution to form methemoglobin.

2. The system of claim 1, where the Fructosyl Amino oxidase directly transfers an electron to the ruthenium hexamine trichloride mediator thus by-passing a peroxide generation step.

3. The system of claim 1, wherein each of the first and second electrochemical test strips includes a first electrode and a second electrode.

4. The system of claim 3, wherein the first and second electrodes form part of an interdigitated electrode.

5. The system of claim 4 wherein one of the first and second electrodes includes a reagent on a surface of one of the first and second electrodes.

6. The system of claim 5, wherein the reagent is painted onto one of the first and second electrodes.

7. The system of claim 1, wherein the first and second test strips are located in a single holder.

8. The system of claim 7, wherein the single holder further includes a third test strip, the third test strip testing for an additional analyte.

9. The system of claim 8, wherein the additional analyte is selected from the group consisting of glucose, ketones, triglycerides, and lactate.

10. The system of claim 8, wherein the single holder further includes a fourth test strip, the fourth test strip testing for a fourth analyte wherein the fourth analyte is selected from the group consisting of glucose, ketones, triglycerides, and lactate and is non-redundant with the additional analyte.

* * * * *